(12) United States Patent
O'Fallon

(10) Patent No.: US 10,449,332 B2
(45) Date of Patent: Oct. 22, 2019

(54) GUIDE WIRE LUER HUB

(71) Applicant: Biosense Webster (Israel) Ltd., Yokneam (IL)

(72) Inventor: Patrick Timothy O'Fallon, Toluca Lake, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 971 days.

(21) Appl. No.: 14/819,382

(22) Filed: Aug. 5, 2015

(65) Prior Publication Data
US 2017/0035996 A1    Feb. 9, 2017

(51) Int. Cl.
*A61M 25/09*      (2006.01)
*A61M 25/00*      (2006.01)

(52) U.S. Cl.
CPC ........ *A61M 25/09* (2013.01); *A61M 25/0009* (2013.01); *A61M 25/0097* (2013.01); *A61M 25/09041* (2013.01); *A61M 2025/091* (2013.01); *A61M 2025/09116* (2013.01); *A61M 2025/09125* (2013.01)

(58) Field of Classification Search
CPC ............ A61M 25/009; A61M 25/0097; A61M 25/09; A61M 25/09041; A61M 2025/091; A61M 2025/09116; A61M 2025/09125
See application file for complete search history.

(56) References Cited

U.S. PATENT DOCUMENTS

| | | |
|---|---|---|
| 4,191,185 A | 3/1980 | Lemieux |
| 4,547,194 A | 10/1985 | Moorehead |
| 4,781,703 A | 11/1988 | Walker et al. |
| 5,320,613 A | 6/1994 | Houge et al. |
| 5,413,561 A | 5/1995 | Fischell et al. |
| 5,470,315 A | 11/1995 | Adams |
| 7,713,260 B2 | 5/2010 | Lessard et al. |
| 7,981,091 B2 | 7/2011 | Root et al. |
| 8,012,145 B2 | 9/2011 | Cawley |
| 2004/0073193 A1 | 4/2004 | Houser et al. |
| 2005/0033237 A1 | 2/2005 | Fentress et al. |
| 2006/0094987 A1 | 5/2006 | van Erp et al. |

FOREIGN PATENT DOCUMENTS

JP     H10216240 A     8/1998

OTHER PUBLICATIONS

EPO Partial European Search Report dated Dec. 14, 2016 for EP Patent Application No. 16182712.6, 7 pages.

*Primary Examiner* — Adam J Eiseman
(74) *Attorney, Agent, or Firm* — Lewis Roca Rothgerber Christie LLP

(57) ABSTRACT

A guide wire luer hub has an elongated hub body with a longitudinal lumen having a plurality of transitions between different lumen sections with different diameters and/or taper angles. The guide wire luer hub is adapted for use with a coaxial guide wire tubing extending from a catheter control handle, where the coaxial tubing has an outer cover or tubing coaxially surrounding a guide wire inner body with a lumen adapted to receive a guide wire, including a guide wire having a floppy, U-bend distal end.

10 Claims, 12 Drawing Sheets

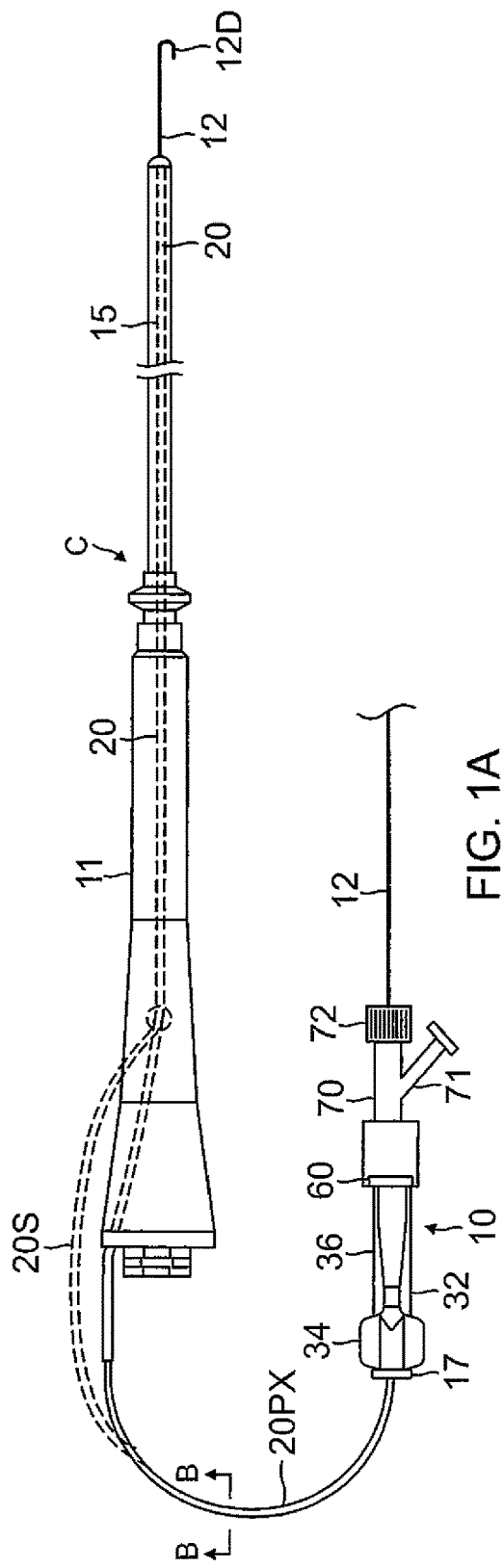
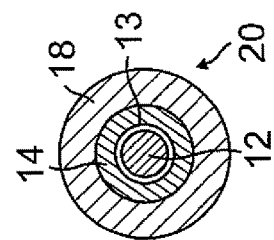
FIG. 1A
FIG. 1B

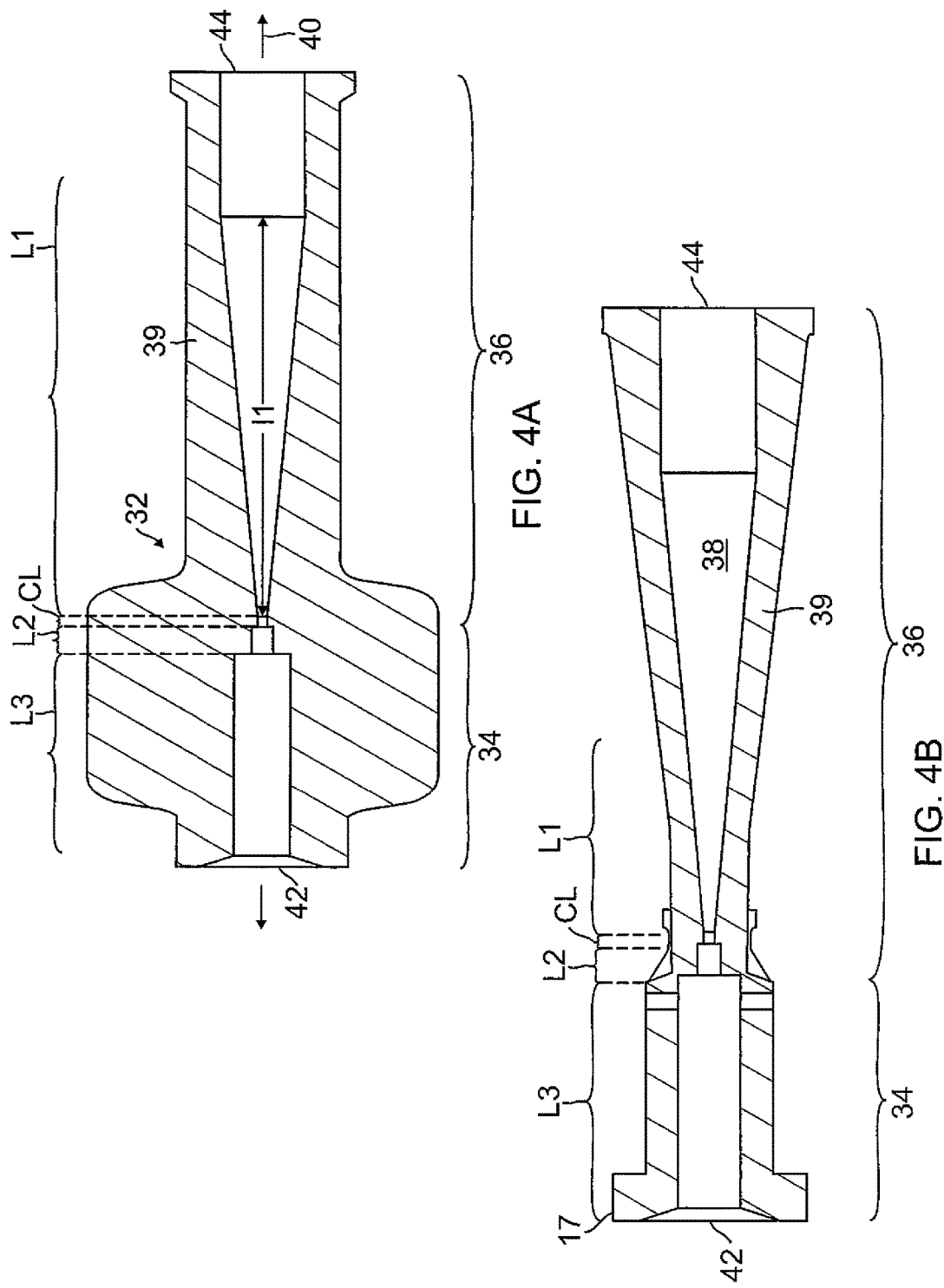

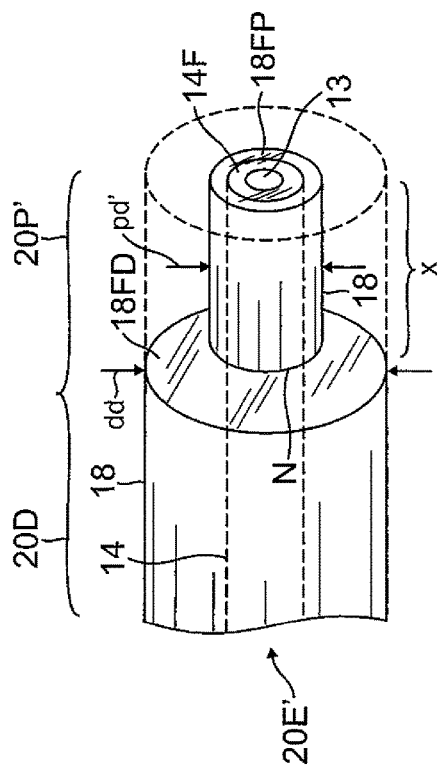
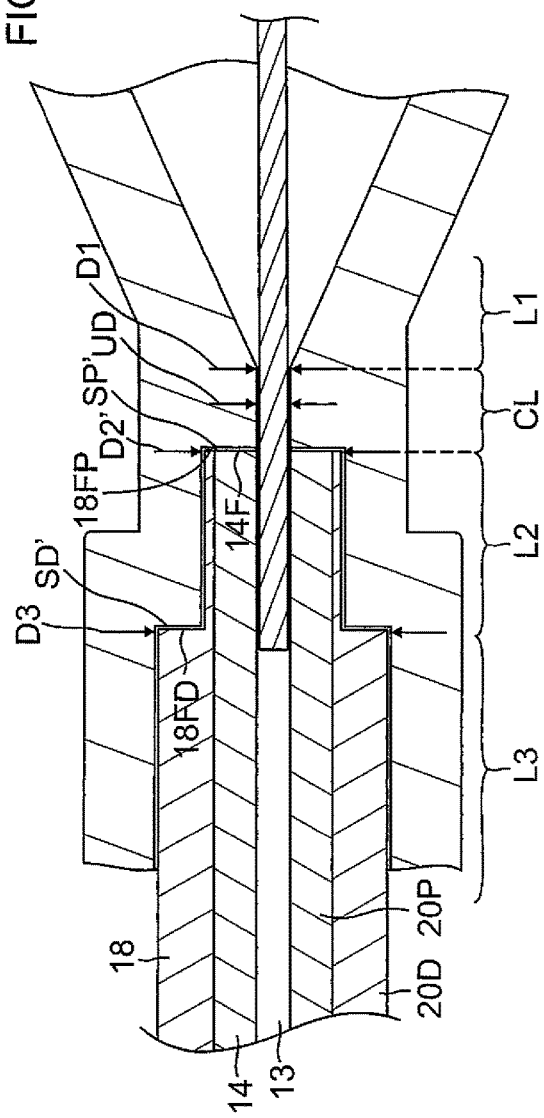
FIG. 5A
FIG. 5B

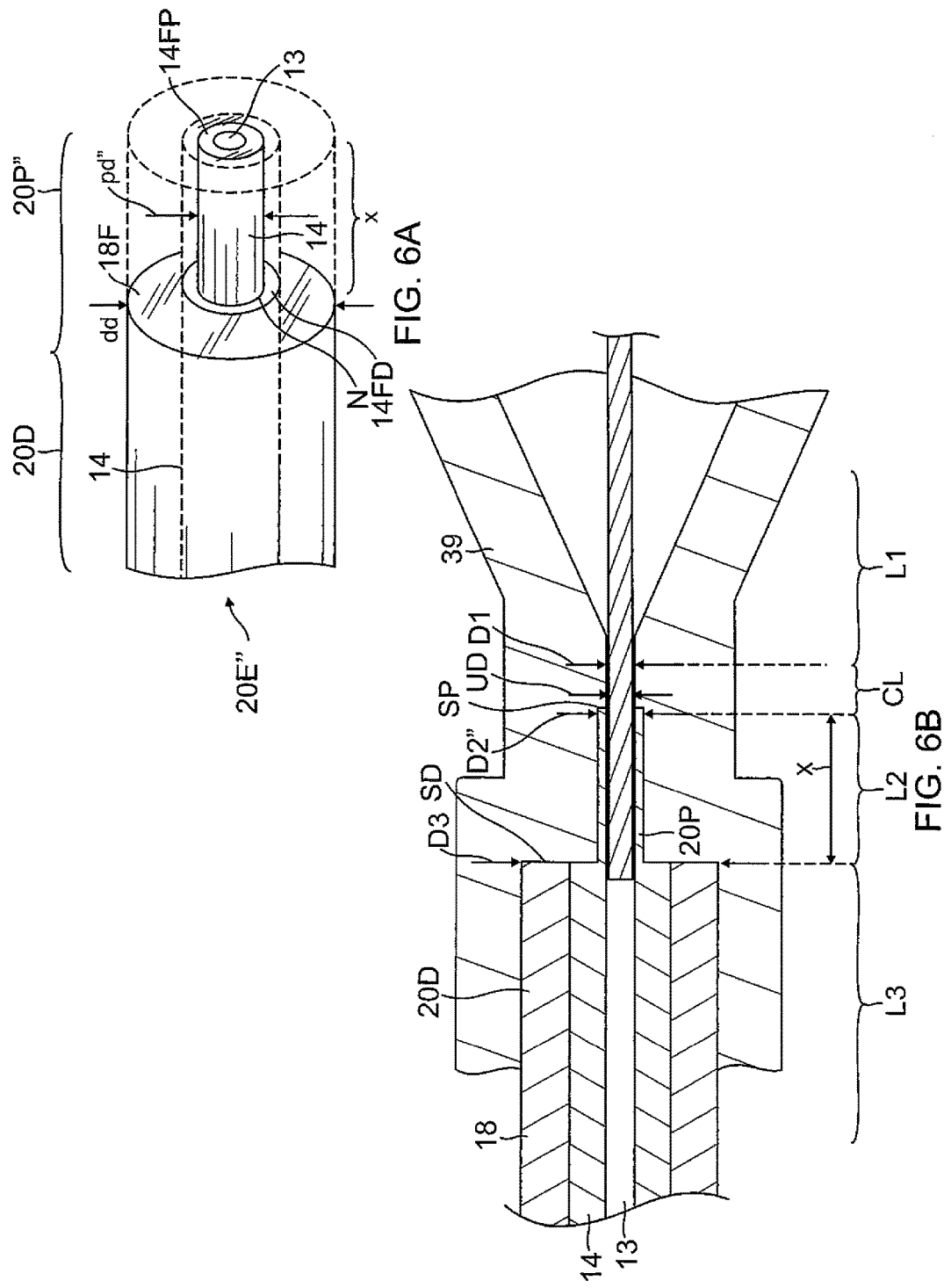

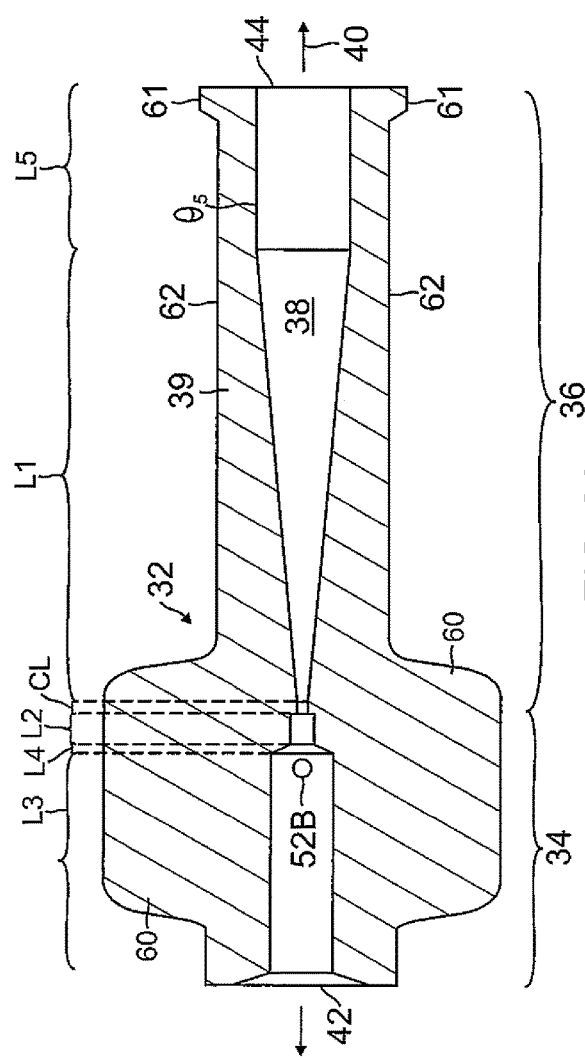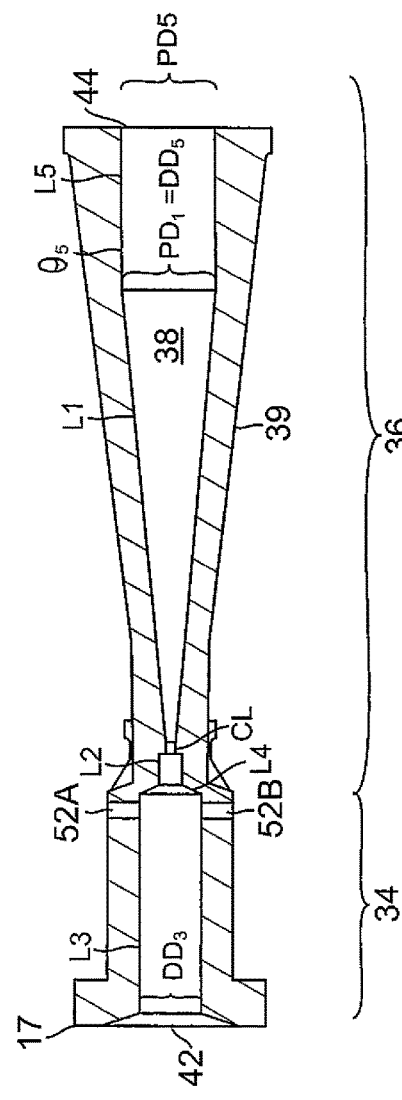
FIG. 8A
FIG. 8B

GUIDE WIRE LUER HUB

FIELD OF INVENTION

The present invention relates to an improved guide wire insertion aid for inserting a guide wire into a lumen of a medical device, including a medical catheter.

BACKGROUND OF INVENTION

Catheters are routinely used for a variety of medical procedures. Catheters are advanced through a patient's vasculature, often guided by a guide wire. Typically, a guided catheter has a lumened guide wire "inner body", and an operator first arranges the guide wire and the catheter by inserting a distal end of the guide wire into a proximal end of the inner body of the catheter. The guide wire is passed through the length of the catheter and then inserted into the patient's body through an introducer. The guide wire is advanced through the vasculature until the distal end of the guide wire reaches a target region, for example, a chamber of the heart or a renal artery. The operator then inserts a distal end of the catheter into the introducer and advances the catheter into the patient's vasculature as the catheter rides over the guide wire following the same pathway defined by the guide wire. At the target region, the catheter can be used in a variety of diagnostic and/or therapeutic procedures, including, for example, mapping and ablation in a chamber or tubular region of the heart, and more recently, ablation in the renal region, including renal arteries, for example, for accessing renal nerves to treat hypertension and other ailments and conditions involving the sympathetic renal nerves.

A guide wire is very thin, typically having a diameter ranging between about 0.0135" and 0.0145", which can make handling a guide wire, and especially threading a guide wire into a comparably-sized lumen of an inner body, a challenging exercise. Threading a guide wire may be particularly difficult where the guide wire has a floppy atraumatic distal portion with a U-bend configuration. As such, some medical users have resorted to inserting the guide wire into catheter inner body in a "backwards" manner, by inserting a proximal end of the guide wire into a distal end of the inner body to avoid having to manipulate the floppy U-bend of the guide wire.

Accordingly, it is desired that a guide wire insertion aid be configured to facilitate the insertion of a guide wire from its distal end into a proximal end of a guide wire inner body, and that the aid facilitate connection with a syringe or other luer connectors so fluid can be introduced into the lumen of the guide wire inner body as needed or desired.

SUMMARY OF THE INVENTION

The present invention includes a guide wire luer hub comprising an elongated hub body with a longitudinal lumen having a plurality of transitions between different lumen sections with different diameters and/or taper angles. The guide wire luer hub is adapted for use with a coaxial guide wire tubing extending from a catheter control handle, where the coaxial tubing has an outer cover or tubing coaxially surrounding a guide wire inner body with a lumen adapted to receive a guide wire.

In some embodiments, a guide wire luer hub is adapted for use with a coaxial tubing having an outer cover surrounding an inner body defining a guide wire lumen with a first diameter. The luer hub has a hub body having a longitudinal axis and a hub lumen extending through the body. The hub lumen has a first lumen section having a second diameter generally equal to or lesser than the first diameter, a proximal lumen section having a distal diameter generally equal to the second diameter, and an elongated distal lumen with a stop between a narrower proximal lumen portion, and a wider distal lumen portion. The hub lumen is adapted to receive a proximal end portion of the coaxial tubing, where the stop is adapted to abut with at least a portion of the outer cover and allow at least a portion of the inner body to extend into the narrower proximal lumen portion, with the guide wire lumen longitudinally aligned with the first lumen section.

In some detailed embodiments, each of the lumen sections is longitudinally aligned with the longitudinal axis of the hub body.

In some detailed embodiments, a larger diameter of the wider distal lumen portion is generally equal to an outer diameter of the outer cover of the coaxial tubing, and a smaller diameter of the narrower proximal lumen portion is generally equal to an outer diameter of the inner body of the coaxial tubing.

In some additional embodiments, a guide wire luer hub has a hub lumen that includes a first proximal lumen section having a distal end diameter D1, a first distal lumen section having proximal end diameter D2, a second distal lumen section having a proximal end diameter D3, and a generally linear centering lumen section between the first distal and the first proximal lumens, the centering lumen section having a uniform diameter UD between its proximal and distal ends, where the diameter D1 is generally equal to the uniform diameter UD, the diameter D2 is greater than the uniform diameter UD, and the diameter D3 is greater than the diameter D2.

In some detailed embodiments where a coaxial guide wire tubing has a main distal portion with diameter dd and a proximal portion with diameter pd, the diameter D3 is generally equal to or slightly less than the diameter dd, and the diameter D2 is generally equal to or slightly less than the diameter pd.

In some detailed embodiments where the coaxial guide wire tubing has an outer cover with diameter dd and an exposed inner body portion with diameter pd, the diameter D3 is generally equal to or slightly less than the diameter dd and the diameter D2 is generally equal to or slightly less than the diameter pd.

In some detailed embodiments, a proximal end of the second distal lumen section is configured to abut with the proximal end face of the outer cover of the coaxial tubing, and a proximal end of the first distal lumen section is configured to abut with a proximal end face of the exposed inner body portion of the coaxial tubing.

In some detailed embodiments, the hub lumen may include a first stop junction between the centering lumen section and the first distal lumen section, configured to abut with a proximal end face of the exposed inner body portion of the coaxial tubing.

In some detailed embodiments, where the coaxial guide wire tubing has an outer cover, an inner body, and a radial notch formation forming a distal face and a proximal face, the hub lumen includes a first stop junction distal of the centering lumen section to abut with the distal face and a second stop junction to abut with the proximal face of the coaxial tubing.

In some detailed embodiments, the inner body of the coaxial tubing has a lumen with a diameter generally equal to the uniform diameter UD, and the lumen of the inner body and the centering lumen section are longitudinally aligned with each other.

In some detailed embodiments, the first proximal lumen section of the hub lumen has a proximal end diameter larger than its distal end diameter.

In some additional embodiments, a guide wire luer hub has a hub body and a hub lumen. The lumen includes a first proximal lumen section having a decreasing diameter from a larger proximal end diameter PDL1 to a smaller distal end diameter DDL1, a first distal lumen section having an increasing diameter from a smaller proximal end diameter PDL2 to a larger distal end diameter DDL2, and a centering lumen section between the first proximal and first distal lumen sections, where each of the lumen sections is axially aligned with a longitudinal axis of the hub, the centering lumen has a uniform diameter UD between its proximal and distal ends, where the uniform diameter UD is generally equal to the distal end diameter DDL1, and the uniform diameter UD is less than the proximal end diameter PDL2 of the first distal lumen section.

In some detailed embodiments, the hub lumen includes a second distal lumen section distal of the first distal lumen section, the second distal lumen section having a proximal end diameter PDL3 greater than the distal end diameter DDL2 of the first distal section.

In some detailed embodiments, the hub is adapted for connection with a coaxial tubing having an outer cover with a diameter dd and an exposed inner body with a diameter pd proximal of the outer cover, and the diameter PDL2 is equal to or slightly less than the diameter pd, and the diameter PDL3 is equal to or slightly less than the diameter dd.

In some detailed embodiments, the hub lumen includes a third distal lumen section between the first and second distal lumen sections, with an increasing diameter between a smaller proximal end diameter PDL4 and a larger distal end diameter DDL4.

In some detailed embodiments, the hub lumen includes a second proximal lumen section proximal of the first proximal lumen section, the second proximal lumen section having a proximal end diameter PDL5 that is greater than a proximal end diameter PDL1 of the first proximal lumen section.

In some detailed embodiments, the hub lumen has a longitudinally linear axis, and at least each of the centering lumen section, the first proximal lumen section, and the first and second distal lumen sections is axially aligned with the longitudinally linear axis.

In some detailed embodiments, at least one radial port is provided in the hub body in communication with the second distal lumen section for application of adhesive between the coaxial guide wire tubing and an inner surface of the hub lumen.

In some detailed embodiments, the hub body has at least one fin and/or at least one ridge to provide structural strength and/or an outer surface on which visual indicia may be positioned.

The present invention also includes methods of manufacturing and assembling a guide wire luer hub and a coaxial guide wire tubing having an outer cover or tubing surrounding a guide wire inner body having a lumen for receiving a guide wire.

In some embodiments, a method of manufacturing a hub body includes forming the hub body with a side wall having a generally uniform thickness between the lumen and an outer surface of the hub body.

In some embodiments, a method of assembling a hub body with a coaxial guide wire tubing having an outer cover surrounding a guide wire inner body, includes removing a portion of the outer cover from a proximal end of the coaxial guide wire tubing to expose a proximal end portion of the guide wire inner body such that a proximal end face of the outer cover and a proximal end face of the inner body are separated by a predetermined distance.

In some embodiments, the method of assembling includes applying adhesive to a proximal end face of the outer cover and a radial surface of the exposed proximal inner body portion, and inserting a proximal end portion of the coaxial tubing into the lumen of the hub at its distal opening until a proximal end face of the guide wire inner tubing abuts with a stop junction between the centering lumen section and the first distal lumen section. The method also includes further comprising applying additional adhesive into the lumen via at least one radial port formed in the hub body in communication with the lumen.

BRIEF DESCRIPTION OF THE DRAWINGS

These and other features and advantages of the present invention will be better understood by reference to the following detailed description when considered in conjunction with the accompanying drawings wherein:

FIG. 1A is a perspective view of a guide wire luer hub of the present invention, in accordance with one embodiment, in use for inserting a guide wire through a catheter.

FIG. 1B is an end cross-sectional view of a guide wire inserted through a guide wire tubing, taken along line B-B of FIG. 1A.

FIG. 4A is a side cross-sectional view of the guide wire luer hub of FIG. 3.

FIG. 4B is a top cross-sectional view of the guide wire luer hub of FIG. 3.

FIG. 5A is a perspective view of a proximal end of a guide wire tubing prepared for use with a guide wire luer hub of the present invention, in accordance with another embodiment.

FIG. 5B is a side-cross-sectional view of the guide wire tubing of FIG. 5A in use with a guide wire luer hub of the present invention.

FIG. 6A is a perspective view of a proximal end of a guide wire tubing prepared for use with a guide wire luer hub of the present invention, in accordance with another embodiment.

FIG. 6B is a side-cross-sectional view of the guide wire tubing of FIG. 6A in use with a guide wire luer hub of the present invention.

FIG. 8A is a side cross-sectional view of a guide wire luer hub of the present invention, in accordance with one embodiment.

FIG. 8B is a top cross-sectional view of the guide wire luer hub of FIG. 8A.

FIG. 11 is a side view of a guide wire.

DETAILED DESCRIPTION OF THE INVENTION

Figure 2:
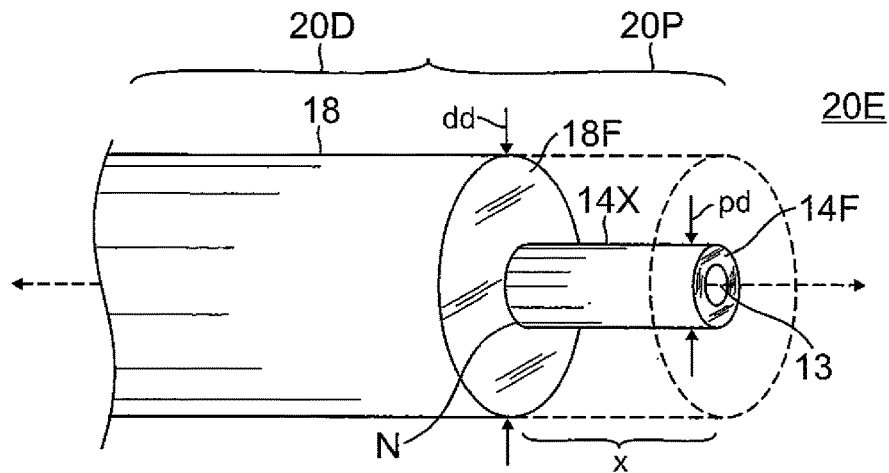
FIG. 2 is a perspective view of a proximal end of a guide wire tubing prepared for use with a guide wire luer hub of the present invention, in accordance with one embodiment.

Some embodiments of the present invention, as shown in FIG. 1A, include a guide wire luer hub 10 configured to facilitate the insertion of a guide wire 12 into a catheter C having a control handle 11, an elongated catheter body 15, and a guide wire tubing 20 which extends through the control handle 11 and through the elongated catheter body 15 coaxially therewith, wherein the elongated catheter body 15 is adapted to enter a patient's vasculature as guided by the guide wire 12. As shown in FIG. 1B, the guide wire tubing 20 comprises an outer nonconductive tubing or cover 18 surrounding a lumened tubing or "inner body" 14 with a lumen 13 through which the guide wire 12 passes. The cover 18, the inner body 14 and the lumen 13 are each concentric about the longitudinal axis of the tubing 20. The guide wire tubing 20 has a proximal portion 20PX that can extend as a side arm 20S partially outside of the control handle (as shown in broken lines in FIG. 1A) or extend through the entire length of the control handle (as shown in solid lines in FIG. 1A).

A proximal end portion 20E of the proximal portion 20PX has a prepared configuration adapted for insertion into and attachment to the hub 10. In some embodiments, as shown in FIG. 2, the proximal end portion 20E has a distal portion 20D with a larger diameter dd, and a proximal portion 20P with a smaller diameter pd where the inner body 14 in the proximal portion 20P is exposed and devoid of the outer cover 18. With the outer cover 18 absent or removed in the proximal portion 20P, the diameter pd is generally equal to the outer diameter of the inner body 14. A proximal end face 14F of the inner body 14 and a proximal end face 18F of the outer cover 18 are separated by a predetermined distance X, and an annular notch N is thus provided at a junction between the portions 20D and 20P.

Figure 3:
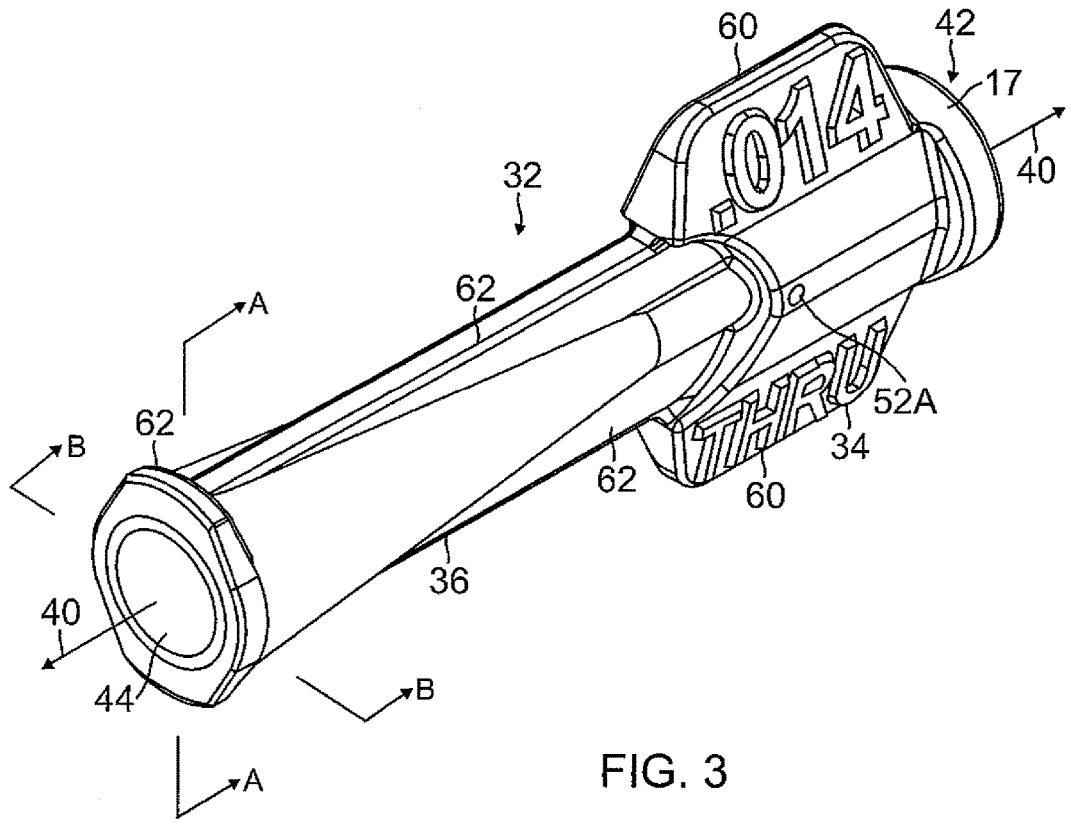
FIG. 3 is a perspective view of the guide wire luer hub of FIG. 1.
Figure 4C:
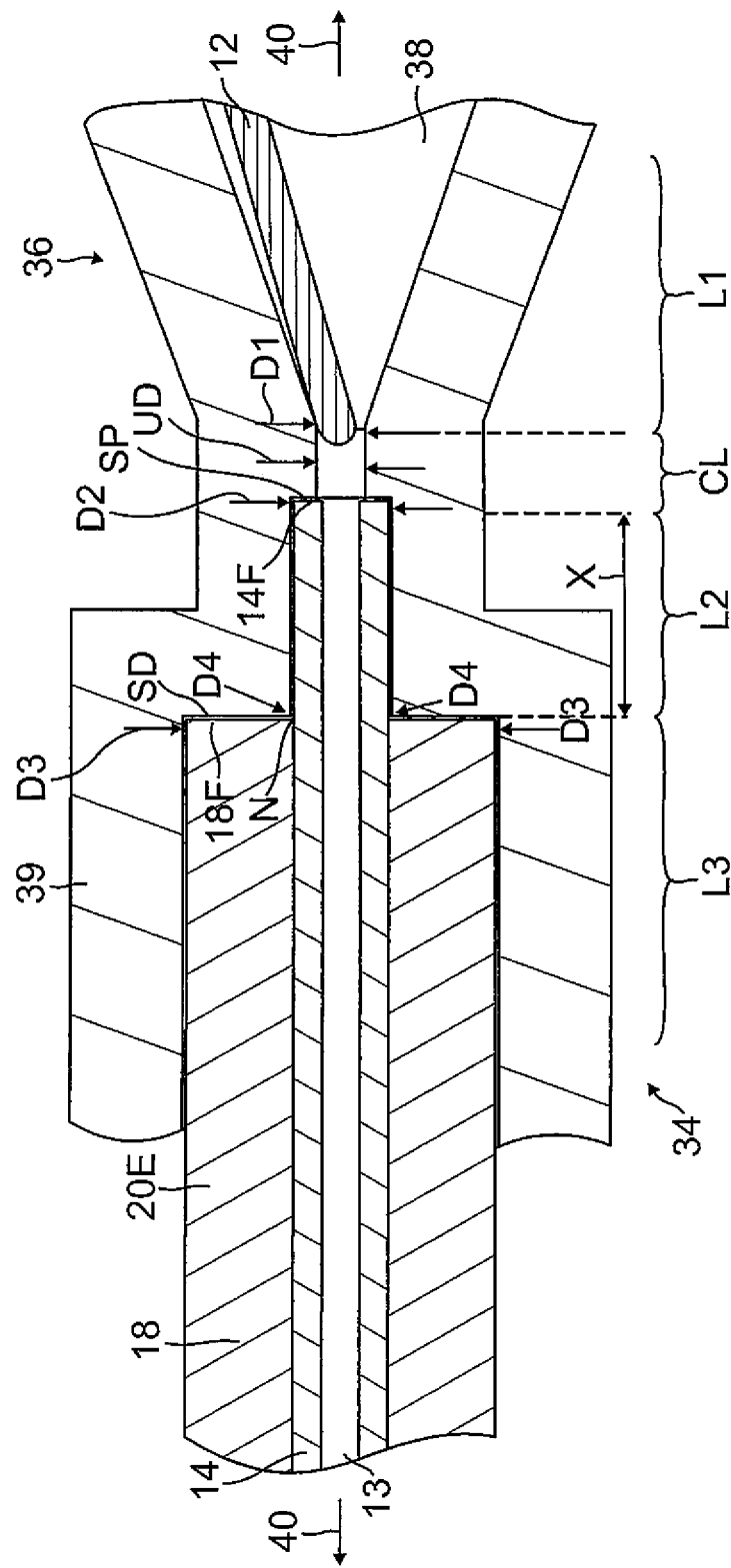
FIG. 4C is a detailed partial side cross-sectional view of a guide wire luer hub of the present invention, according to one embodiment.

In some embodiments, as shown in FIGS. 3, 4A and 4B, the guide wire luer hub 10 has an elongated body 32 having a shorter distal portion 34, a longer proximal portion 36, and a lumen 38 extending along a longitudinal axis 40 defined by surrounding side wall 39, between a distal opening 42 and a proximal opening 44. As best shown in FIG. 4C, the distal portion 34 is configured to receive the proximal end 20E of the coaxial tubing 20. The proximal portion 36 is configured to feed the guide wire 12 into the proximal end 20E of the coaxial tubing 20. In that regard, the lumen 38 of the hub 10 has multiple sections of different configurations, including different inner diameters, different lengths, and/or conical taper angles, in accordance with a feature of the present invention.

The lumen 38 includes at least a first proximal lumen section L1 having a distal end diameter D1, a first distal lumen section L2 having a proximal end diameter D2 and a distal end diameter D4, and a generally linear centering/alignment lumen section CL therebetween having a generally uniform diameter UD between its proximal and distal ends. The lumen 38 also include a second distal lumen section L3 having a proximal end diameter D3. The centering lumen section CL may have the smallest diameter along the length of the lumen 38 so as to center and align the guide wire 12 for entry into the lumen 13 of the inner body 14. Structural relationships of the lumen 38 include:

the diameter UD is equal or lesser than the diameter of the lumen 13 of the coaxial tubing 20 (which is understood to be greater than the diameter of the guide wire 12 in order to receive and pass the guide wire 12 therethrough);

the distal end diameter D1 is generally equal to the uniform diameter UD;

the proximal end diameter D2 is greater than the uniform diameter UD and also generally equal to or slightly less than the diameter pd of the coaxial tubing 20; and the proximal end diameter D3 is greater than the distal end diameter D4 thereby forming a stop SD, and the diameter D3 also generally equal to or slightly less than the diameter dd of the coaxial tubing 20.

Each of the lumen sections L1, L2, L3 and CL is on-axis and longitudinally aligned with a longitudinal axis 40 of the lumen 38. The lumen sections L2 and L3 are configured (for example, in terms of diameter and/or length) to position the proximal end portion 20E of the coaxial tubing so that its lumen 13 is in longitudinal alignment with the centering lumen section CL. As such, the lumen 13 is optimally positioned to receive a distal end of guide wire 12 advancing distally from the lumen section L1, with the transition between the lumen 13 and lumen section CL being advantageously continuous and smooth without any protruding edges that may catch and obstruct the distal end of the guide wire 12 from advancing into the lumen 13.

When the proximal end 20E of the coaxial tubing 20 is received in the distal portion 34 of the hub body 32 during connection and assembly of the coaxial tubing 20 and the hub 10, as shown in FIG. 4C, the proximal end face 18F of the cover 18 is positioned at a proximal end of the lumen section L3 such that the notch N of the tubing 20 abuts with a distal stop SD formed in the sidewall 39 at a junction between the different diameters of the lumen sections L2 and L3. Moreover, the proximal end face 14F of the inner body 14 is positioned at a proximal end of the lumen section L2 which has a length generally equal to the distance X (FIG. 2) between the proximal end faces 18F and 14F of the proximal end 20E of the coaxial tubing 20. A proximal stop SP abutting the proximal end face 14F of the tubing 20 is formed in the sidewall 39 at a junction between the different diameters of the lumen sections CL and L2. The distal stop SD has a radial dimension generally equal to or slightly less than the sidewall thickness of the outer cover 18, and the proximal stop SP has a radial dimension generally equal to or slightly less than the sidewall thickness of the inner body 14.

It is understood that the radial dimensions of stops SD and SP may be varied in accordance with varied diameter dd and/or pd of the proximal end portion 20E, so long as the lumen 13 remains on-axis and concentric with the longitudinal axis of the coaxial tubing 20. For example, the diameter dd and/or pd may be varied depending on the thickness of the layer of outer cover 18 and/or inner body 14 remaining in the proximal end portion 20E. In alternate embodiments, as shown in FIGS. 5A and 5B, a proximal end portion 20E' of the coaxial tubing 20 has a proximal portion 20P' with a diameter pd' that is larger than the aforementioned diameter pd. The proximal portion 20P' has a partial layer of the outer cover 18 remaining on the inner body 14 such that the proximal end face 14F is surrounded by and coplanar with a partial proximal end face 18FP that is proximal of a partial distal end face 18FD by the distance X. A diameter D2' of the first distal lumen L2 is generally equal or slightly less than the diameter pd' of the proximal portion 20P'. The diameter pd' (>diameter pd) results in radial stops SD' and SP' with different radial dimensions from those of the aforementioned radial stops SD and SP.

In other alternate embodiments, as shown in FIGS. 6A and 6B, a proximal end portion 20E'' of the coaxial tubing 20 has a proximal portion 20P''' with a diameter pd'' that is smaller than the aforementioned diameter pd of proximal portion 20P. The proximal portion 20P''' is without the outer cover 18 and also without an outer layer of the inner body 14 such that the proximal end face 18F surrounds and is coplanar with a partial distal end face 14 FD that is distal of a partial proximal end face 18FP by distance X. A diameter D2'' is generally equal to or slightly lesser than the smaller diameter pd' of the proximal portion 20P'. The diameter D2'' results in distal and proximal radial stops SD'' and SP'' with different radial dimensions than those of the aforementioned radial stops SD and SP.

In some embodiments, the distance X may range between about 0.020" and 0.060", and preferably between about 0.035" and 0.045". In some embodiments, the length of the centering lumen section CL may range between about 0.000" and 0.025", and preferably between about 0.012" and 0.017".

Figure 7:
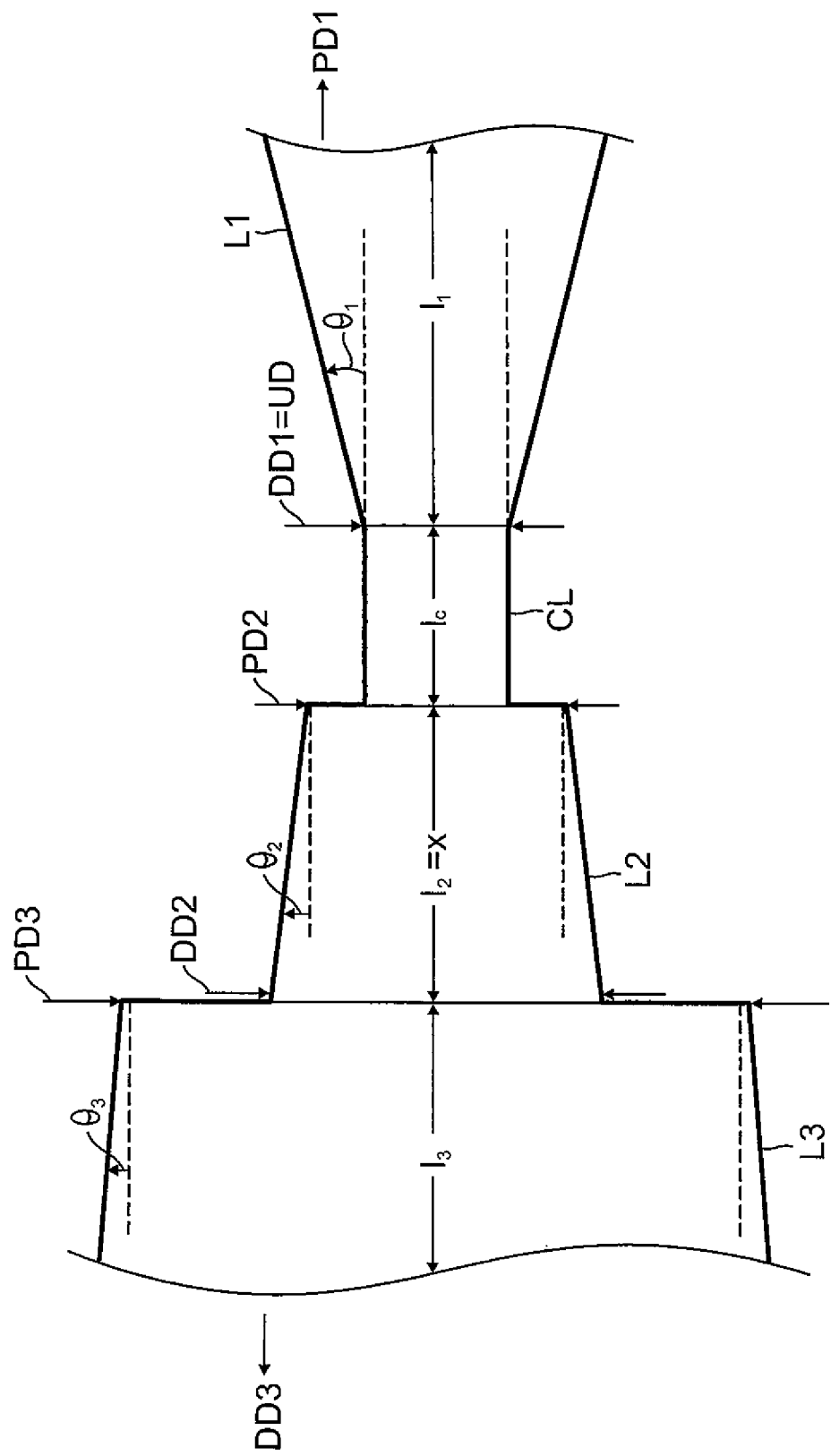
FIG. 7 is a schematic cross-sectional view of a hub lumen of a guide wire luer hub of the present invention, in accordance with one embodiment.
Figure 8C:
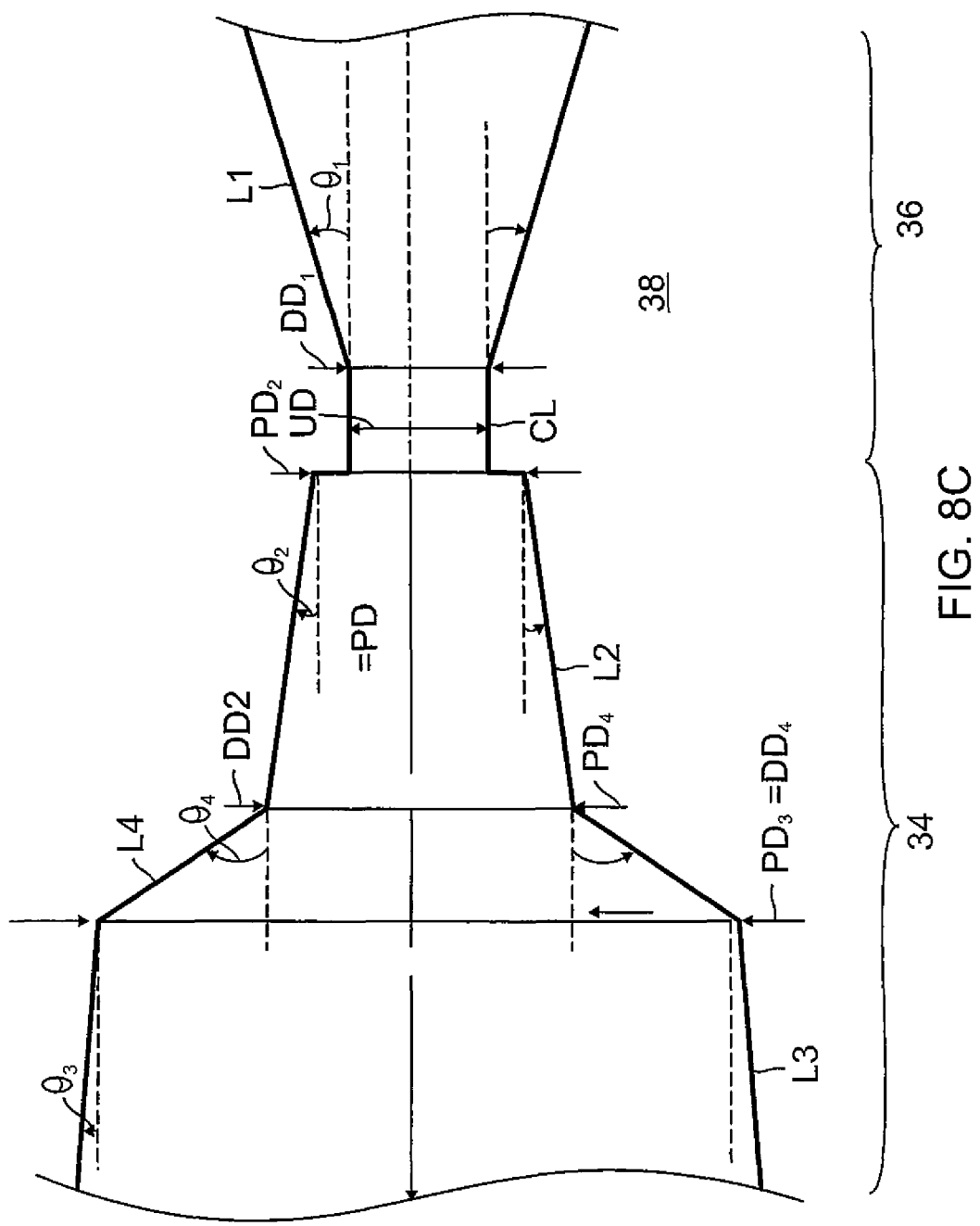
FIG. 8C is a schematic side cross-sectional view of the hub lumen of the guide wire luer hub of FIG. 8A and FIG. 8B.
Figure 8D:
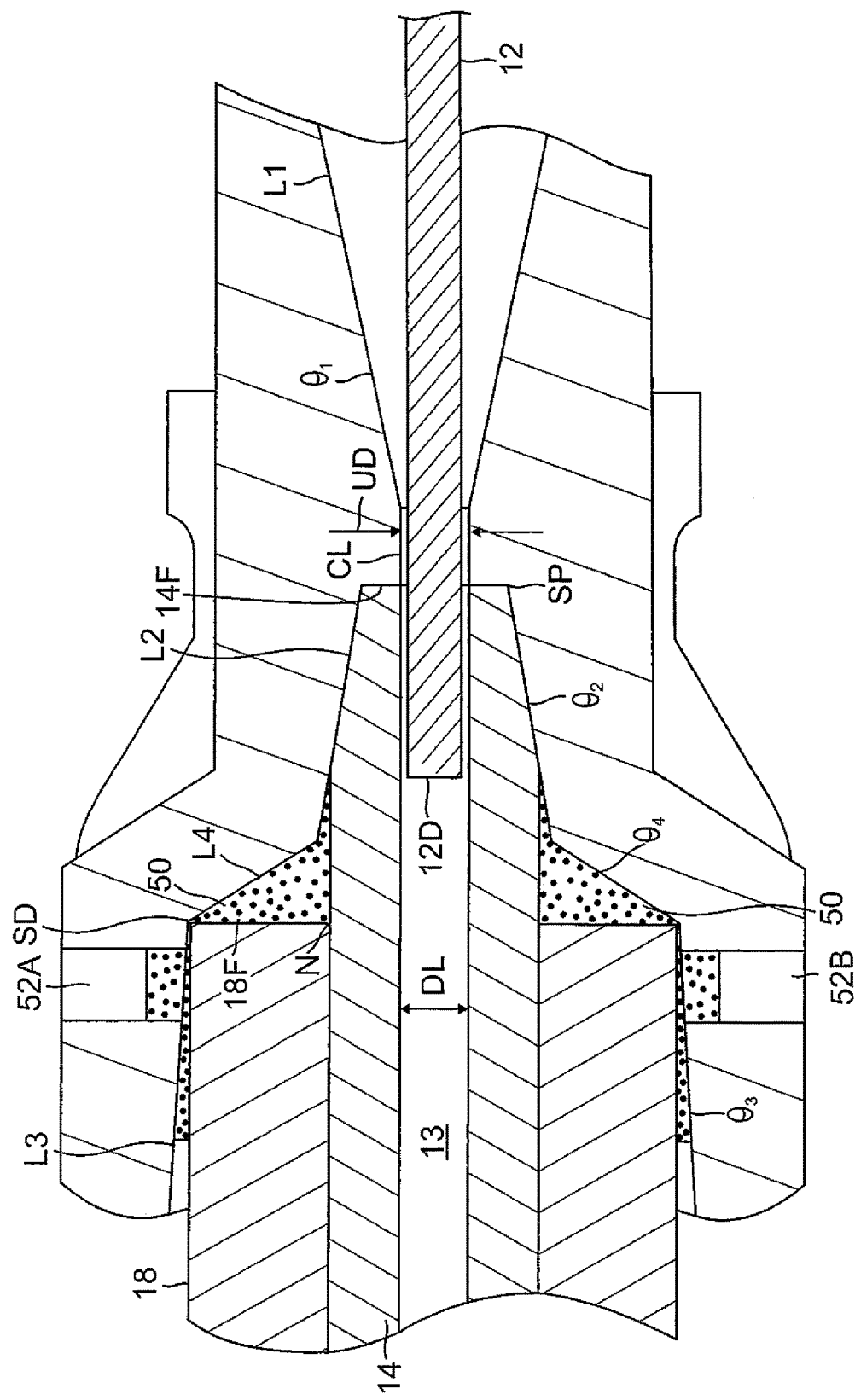
FIG. 8D is a side cross-sectional view of the guide wire luer hub of FIG. 8A and FIG. 8B, with a guide wire passing into a guide wire tubing received in the luer hub, in accordance with one embodiment.

Whereas the centering lumen section CL has a uniform diameter UD along its length, the other lumen sections may have changing diameters defining taper angles. In some embodiments, as shown in FIG. 7, the first proximal lumen section L1 has a decreasing diameter from a larger proximal end diameter to a smaller distal end diameter defining decreasing taper angle θ1. The first proximal lumen section L1 with the decreasing taper angle θ1 and length l1 is configured as a funnel or chute to channel the guide wire 12 into the centering lumen section CL.

The first distal lumen section L2 has an increasing diameter from a smaller proximal end diameter to a larger distal end diameter defining increasing taper angle θ2. The second distal lumen section L3 has an increasing diameter from a smaller proximal end diameter to a larger distal end diameter defining increasing taper angle θ3.

In some embodiments, the centering lumen section CL is configured as the narrowest and shortest section of the lumen sections. The section CL has a uniform diameter UD which is generally equal to or lesser than a diameter of the lumen 13 of the coaxial tubing 20 so the guide wire 12 does not catch the inner body 14 when entering the lumen 13. The centering lumen section CL is on-axis with the lumen 38 and/or the longitudinal axis 40 of the hub body 32 and has the uniform diameter UD between its distal and proximal ends to ensure that the distal end 12D of the guide wire 12 enters the lumen 13 straight and on-axis.

The length $l_1$ of the first proximal lumen section L1 may be a large multiple of the length $l_c$ of the section CL, ranging between about 35 times and 45 times greater, preferably between about 38 and 43 times greater, and more preferably about 40 times greater, so that the decreasing taper angle $\theta_1$ is sufficiently gradual to allow the distal end of the guide wire 12 to funnel into the lumen section CL from the lumen section L1.

The first distal lumen section L2 has a proximal end diameter PD2 greater than the uniform diameter UD. In some embodiments, the proximal end diameter PD2 may be slightly smaller than the diameter pd (or pd' or pd'') of the proximal portion 20P of the coaxial tubing 20 so that the proximal portion 20P has a snug fit in the lumen section L2 to better ensure that the portion 20P is on-axis or centered in the lumen section L2 and that the lumen 13 is longitudinally aligned with the centering lumen section CL. The length $l_2$ of the lumen section L2 is generally equal with the distance X of the proximal portion 20P.

The second distal lumen section L3 has a proximal end diameter PD3 greater than the diameter DD2. The proximal end diameter PD3 may be slightly smaller than the diameter dd of the distal portion 20D of the coaxial tubing 20 so that the distal portion 20D has a snug fit in the lumen section L3 to better ensure that the portion 20D is centered in the lumen section L3.

More additional embodiments are shown in FIGS. 8A-8D, where the lumen 38 includes additional lumen sections, including an additional distal lumen section L4 extending between and connecting the first and second distal lumen sections L2 and L3. The lumen section L4 has a proximal end diameter PD4 which is generally equal to the distal end diameter DD2, a distal end diameter DD4 which is generally equal to the proximal end diameter PD3.

When the distal lumen section L2 and L3 receive the proximal end portion 20E of the coaxial tubing 20, the taper angle θ4 of the lumen section L4 defines a gap or void region around the notch N of the tubing 20 which can be advantageously filled with adhesive 50 to affix the proximal end portion 20E in the hub 10. In some embodiments, one or more radial ports 52A and 52B are formed in the sidewall 39 of the hub body 32 to allow application or injection of adhesive 50 into the void region. The taper angles θ2 and θ3 facilitate the spreading and seeping of adhesive to areas in the distal lumen sections L2 and L3 proximal and distal of the notch N.

The hub lumen 38 may also include a second proximal lumen section L5. At or near the proximal opening 42, the surrounding side wall 39 of the hub body 32 is configured as a standard luer connector (e.g., female luer lock) with outer flanges 61 (FIG. 8A) to allow the proximal end of the hub 10 to be connected to another device, for example, a syringe or other luer connectors.

Shown below in Table 1 are the dimensions of the lumen sections of the present invention, in accordance with some embodiments:

TABLE 1

| Lumen Section | Length Range Length | Distal Diameter Range DD | Proximal Diameter Range PD | Angle Range Preferred Angle |
|---|---|---|---|---|
| 1st proximal lumen L1 | $l_1$ = 0.550"-0.650" <br> l1 = 0.605" | DD1 = 0.0165"-0.0185" <br> DD1 = 0.0175" | PD1 = 0.145"-0.165" <br> PD1 =.= 0.151" | Θ1 = 11.4-12.4 degrees <br> Θ1 = 11.9 degrees |

TABLE 1-continued

| Lumen Section | Length Range Length | Distal Diameter Range DD | Proximal Diameter Range PD | Angle Range Preferred Angle |
|---|---|---|---|---|
| centering lumen CL | $l_c$ = 0.010"-0.020" $l_c$ = 0.015" | DDc = 0.0165"-0.0185" DDc = 0.0175 | PDc = DDc PDc = DDc | n/a |
| 1st distal lumen L2 | $l_2$ = 0.000"-.050" $l_2$ = 0.0413" | DD2 = 0.025"-0.035" DD2 = 0.0322" | PD2 = 0.020"-0.030" PD2 = 0.025" | Θ2 = 4-6 degrees Θ2 = 5 degrees |
| 2nd distal lumen L3 | $l_3$ = 0.250"-0.350" $l_3$ = 0.319" | DD3 = 0.091"-0.101" DD3 = .096" | PD3 = 0.085"-0.095" PD3 = .0904" | Θ3 = 0.5-1.5 degrees Θ3 = 1 degree |
| 3rd distal lumen L4 | $l_4$ = 0.000"-0.020" $l_4$ = 0.0106" | DD4 = PD3 DD4 = PD3 | PD4 = DD2 PD4 = DD2 | Θ4 = 65-75 degrees Θ4 = 70 degrees |
| 2nd proximal lumen L5 | $l_5$ = 0.290"-0.305" $l_5$ = 0.295" | DD5 = 0.145"-0.156" DD5 = PD1 | PD5 = 0.155-0.1875" PD5 = 0.169 | Θ5 = 1.5-2 degrees Θ5 = 1.715 degrees |

As shown in FIGS. 4A and 4B, the sidewall 39 has (or at least is initially formed with) a generally uniform thickness throughout the hub body 32 with the exception of fins 60 and ridges 62, as described further below. In some embodiments, the hub body 32 is manufactured integrally as a single body by any suitable process from any suitable material, for example, injection molding processing with plastics including, polycarbonate or ABS or similar. In some embodiments, the material is generally transparent with minimal or no UV inhibitors to allow for UV light curing. The transparency also allows viewing of the mating of the coaxial tubing 20 with the inner surface of the lumen sections L2, L3 and/or L4 and any fluid flowing through the lumen 38 of the hub 10. In any case, where the process requires curing of the underlying material, the sidewall 39 is advantageously formed with a generally uniform thickness in particular in the region of the lumen sections L1, CL and L2 to minimize shrinkage and deformation during curing. It is understood and appreciated that given the size and scale of the hub 10 and its structural features and dimensions, the hub and its manufacturing process and equipment have strictly limited engineering tolerances in order for the hub to perform its intended function of readily guiding the guide wire 12 into the lumen 13 of the guide wire inner body 14. By having a generally uniform thickness, the sidewall 39 and the lumen sections can better maintain their size and configuration during curing of the hub body 32.

The exceptions to the generally uniform thickness of the sidewall 39 include the fins 60 and the ridges 62, as shown in FIGS. 3 and 4A, which provide structural strength to the body 32. The fins 60 and the ridges 62 lie along a diameter of the lumen 38. In the illustrated embodiment, the fins 60 are configured to span across at least the lumen sections L1, CL and L2, L3 and L4, with lumen sections L1, CL and L2 being possibly the weakest structural portions of the hub body 32. Advantageously, outer surface of the fins may display visual indicia indicating the size of the guide wire 12 for which the hub 10 may be used (see FIG. 3).

In some embodiments of the present invention, prior to the proximal end 20E of the coaxial tubing 20 being inserted into the lumen sections L2, L3 and L4, a distal end of a substitute guide wire 12' is inserted into the lumen 13 at the proximal end of the coaxial tubing 20 as a temporary plug in the lumen 13. A layer of the adhesive 50 is applied to the proximal end 20E, including an end face of the distal portion 20D and a radial surface of the proximal portion 20P, 20P' and 20P" (see FIGS. 2, 5A and 6A). A proximal end of the substitute guide wire 12' is then inserted into the lumen 38 via the distal opening 42 of the hub body 32, followed by the proximal end portion 20E of the coaxial tubing 20 which is inserted with a degree of force until the notch N abuts with the distal stop SD and a proximal end face 14F of the guide wire inner body abuts with the proximal stop SP between the different diameters of the lumen sections CL and L2 (see FIGS. 4C and 8D). The taper angles Θ2 and Θ3 of the distal lumen sections L2 and L3 help the adhesive 50 to spread and fill in any voids in the lumens L2 and L3 between the outer surfaces of the guide wire tubing 14 and the cover 18. Additional adhesive may be introduced via the radial ports 52, for example, by a syringe. Such additional adhesive may spread proximally and also distally of the radial ports 52. Transparency of the hub body 32 allows viewing of insertion and mating of the coaxial tubing 20P in the lumens L2, L3 and L4 and the injection and spreading of adhesive in those lumens. After the adhesive 50 has set, the substitute guide wire 12' is removed from the lumen 13 of the guide wire tubing 14 via the proximal opening 44 of the hub body 32.

Figure 9:
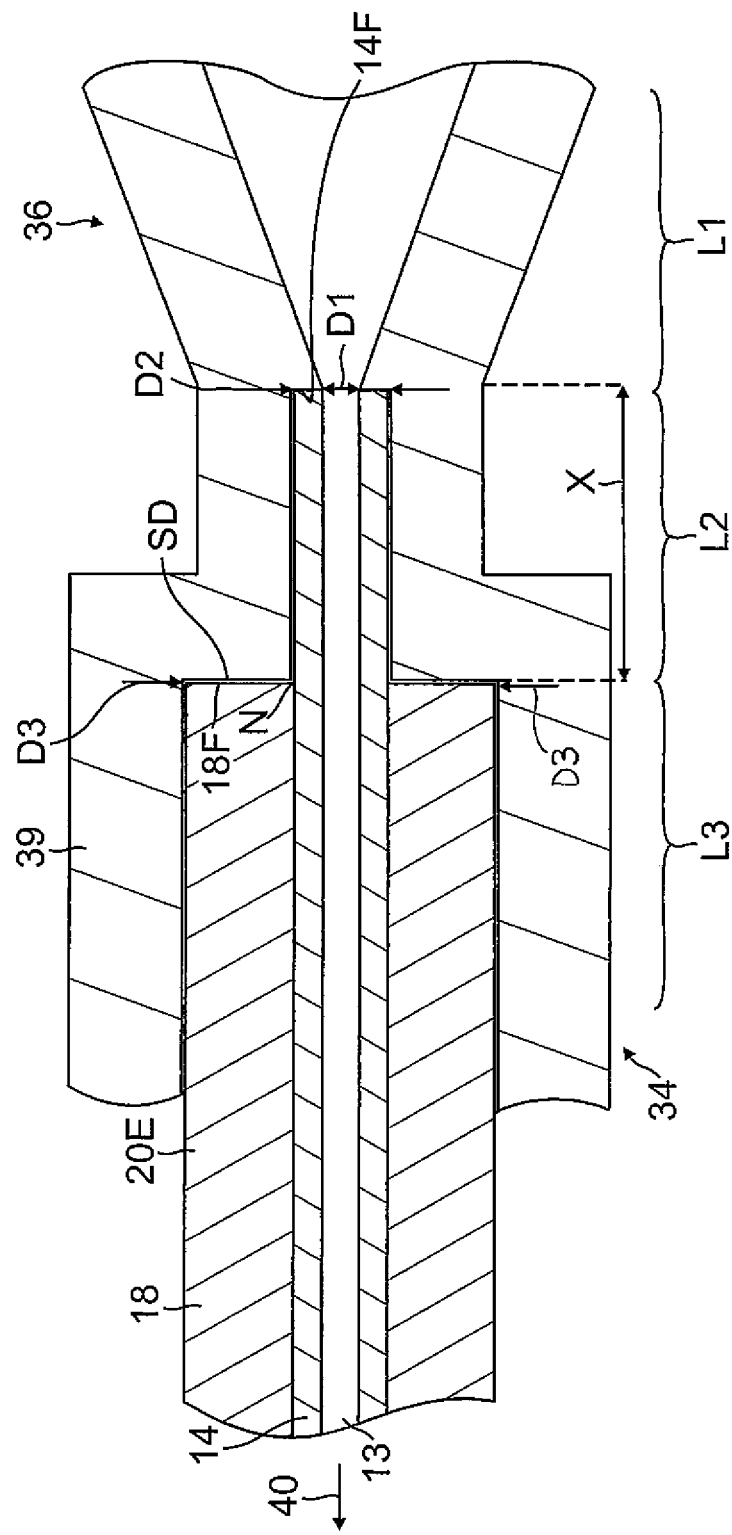
FIG. 9 is a side cross-sectional view of a guide wire luer hub of the present invention, in accordance with one embodiment.

In additional embodiments of the present invention as shown in FIG. 9, the lumen sections L1 and L2 are in direct communication with each other, without the lumen section CL extending therebetween.

Figure 10A:
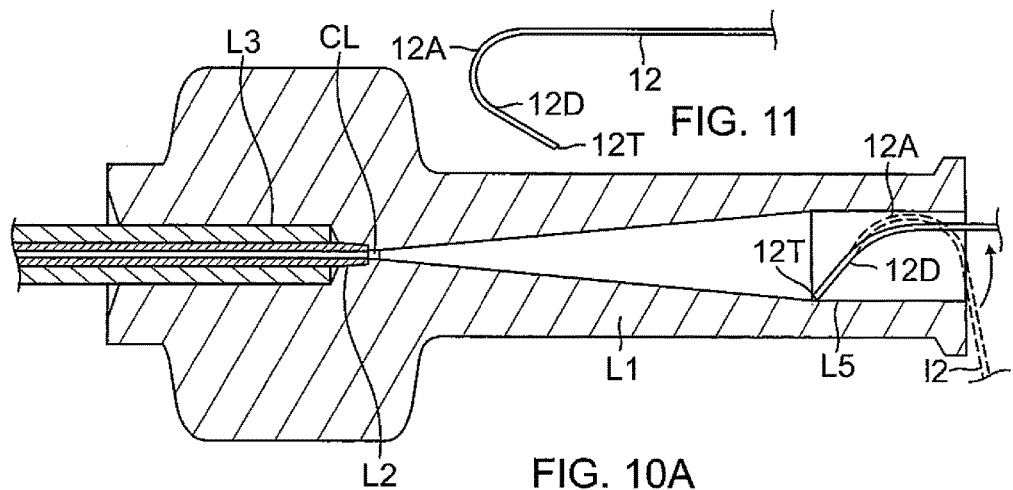
FIGS. 10A-10C are side cross-sectional views of a guide wire luer hub with a hub lumen in communication with a guide wire tubing, illustrating entry of a guide wire into a hub lumen, and a lumen of the guide wire tubing.
Figure 10B:
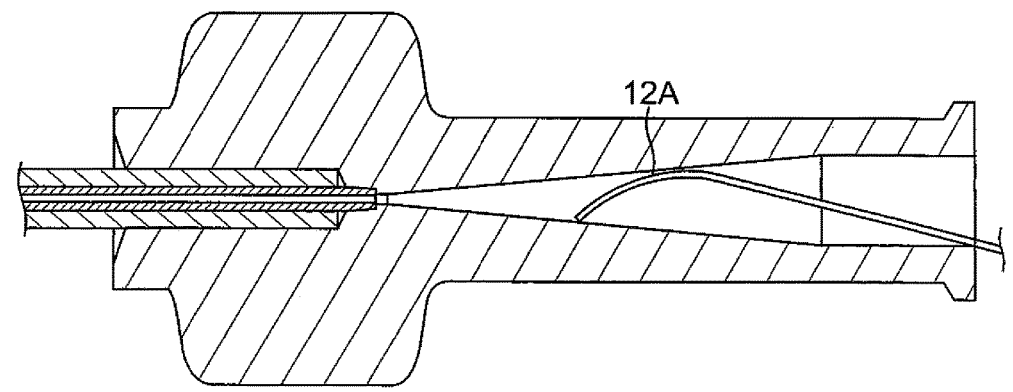
Figure 10C:
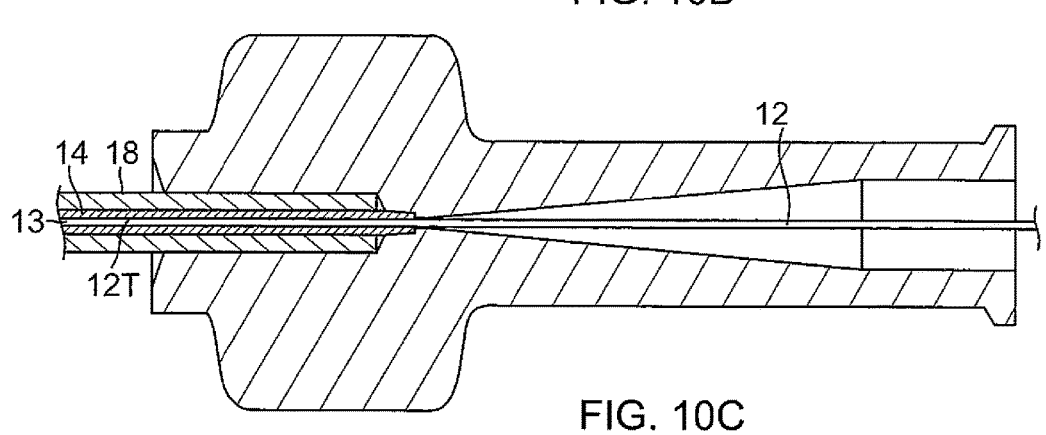

In use, the hub 10 having been affixed to the proximal end 20E of the coaxial tubing 20 is ready to receive the guide wire 12, as shown in FIGS. 10A-10C. The guide wire has a distal curled U-bend end 12D, as shown in FIG. 11. The hub is suitable for use with a guide wire, for example, having a diameter of about 0.014 inch and a distal curl length of about 1.5 cm with a curl radius of about 7.0 mm.

To insert the guide wire, the U-bend end 12D is temporarily straightened by the user who positions the guide wire 12 at least generally perpendicular to, if not oppositely parallel with, the hub 10 to initially hook the U-bend end 12D in the proximal opening 44 of the hub 10 (as shown in broken lines in FIG. 10A). The user then pivots the guide wire 12 toward the longitudinal axis of the hub 10 to open the U-bend end 12D by leveraging an apex portion 12A against an inner surface of the lumen 38 (as shown in solid lines in FIG. 10A). Because of a low-friction inner surface of at least the lumen sections L1 and L5 (if not the entire length of the lumen 38) and the taper of the lumen section L1, the user is able to advance the guide wire distally with the distal tip end 12T and the apex portion 12A sliding along the inner surface toward the lumen section CL with the U-bend end 12D generally straight and not resuming its full curl.

As the guide wire is further advanced distally by the user, the distal tip end 12T is funneled by the tapered lumen section L1 into the lumen section CL whose diameter is sized and centered so as to feed the distal tip end 12T into the lumen 13 of the guide wire inner body 14 smoothly without hitting or catching the inner body 14. With the guide wire 12 successfully fed into the inner body 14 and hence into the catheter, the guide wire 12 is then further passed through the lumen 13 until it passes the distal end of the guide wire inner body 14 and the distal end of the catheter body 15, at which the distal end 12D reassumes its U-bend shape. Having been passed through the catheter C, the guide wire 12 (as shown in FIG. 1) is ready to be inserted into a patient's body, for example, via an introducer, as known in the art. The distal end of the guide wire is advanced through the patient's vasculature until it reaches a target region, such as a renal artery. The elongated catheter body 15 is then advanced through the patient's vasculature, guided by the guide wire 12, until the distal tip of the catheter body 15 reaches the target region. As needed or desired, fluid may be introduced into the lumen 13 of the guide wire inner body 14 via a side arm 71 of a hemostasis valve 70, e.g., a Tuohy Borst, mounted on the outer flange 60 of the female luer lock at the proximal opening 44 of hub body 32. The valve 70 may include gripper 72 adapted to lock and hold the guide wire 12.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention, and that the drawings are not necessarily to scale. Moreover, it is understood that any one feature of an embodiment may be used in lieu of or in addition to feature(s) of other embodiments. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A guide wire luer hub for use with a coaxial tubing having an outer cover surrounding an inner body with a guide wire lumen of diameter DGW, comprising:
    a hub body having a longitudinal axis; and
    a hub lumen extending through the body, the hub lumen having:
        a centering lumen section having a diameter DCL generally equal to or lesser than the diameter DGW;
        a proximal lumen section having a distal diameter generally equal to the diameter DCL;
        a radially wider distal lumen section and a radially narrower distal lumen section, the radially wider distal lumen section being distal of the radially narrower distal lumen section;
        a distal stop at a junction between the radially wider and radially narrower distal lumen sections, the distal stop comprising a distal annular notch configured to abut with at least a portion of the outer cover and allow at least a portion of the inner body to extend into the radially narrower distal lumen section with the guide wire lumen longitudinally aligned with the centering lumen section; and
        a proximal stop at a junction between the radially narrower distal lumen section and the centering lumen section, the proximal stop comprising a proximal annular notch configured to abut with at least a portion of the inner body.

2. The luer hub of claim 1, wherein each of the lumen sections is longitudinally aligned with the longitudinal axis of the hub body.

3. The luer hub of claim 1, wherein a larger diameter of the radially wider distal lumen section is generally equal to an outer diameter of the outer cover of the coaxial tubing, and a smaller diameter of the radially narrower distal lumen section is generally equal to an outer diameter of the inner body of the coaxial tubing.

4. A guide wire luer hub comprising:
    a hub body having a longitudinal axis;
    a lumen extending through the hub body, the lumen including:
        a first proximal lumen section having a distal end diameter D1;
        a first distal lumen section having a proximal end diameter D2;
        a second distal lumen section having a proximal end diameter D3; and
        a centering lumen section between the first proximal lumen section and the first distal lumen section, having a uniform diameter UD between its proximal and distal ends,
    each of the lumen sections is axially aligned with the longitudinal axis,
    the diameter D1 is generally equal to the uniform diameter UD,
    the diameter D2 is greater than the uniform diameter UD such that the hub comprises a proximal stop comprising a proximal annular notch at a junction between the first distal lumen section and the centering lumen section, and
    the diameter D3 is greater than the diameter D2 such that the hub comprises a distal stop comprising a distal annular notch at a junction between the first distal lumen section and the second distal lumen section.

5. The luer hub of claim 4, wherein the hub is configured for use with a coaxial guide wire tubing having a distal portion with a larger diameter dd and a proximal portion with a smaller diameter pd, the diameter D3 is equal to or slightly less than the diameter dd and the diameter D2 is generally equal to or slightly less than the diameter pd.

6. The luer hub of claim 4, wherein the hub is configured for use with a coaxial guide wire tubing having an outer cover with a diameter dd and an exposed inner body proximal portion with a diameter pd, the diameter D3 is generally equal to or slightly less than the diameter dd and the diameter D2 is generally equal to or slightly less than the diameter pd.

7. The luer hub of claim 6, wherein a proximal end of the second distal lumen section is configured to abut with a proximal end face of the outer cover, and a proximal end of the first distal lumen section is configured to abut with a proximal end face of the exposed inner body proximal portion.

8. The luer hub of claim 6, wherein the proximal stop is configured to abut with a proximal end face of the exposed inner body proximal portion.

9. The luer hub of claim 6, wherein the exposed inner body proximal portion has a lumen with a diameter that is generally equal to the uniform diameter UD, and the lumen of the exposed inner body proximal portion and the centering lumen section are longitudinally aligned with each other.

10. The luer hub of claim 4, wherein the first proximal lumen section has a proximal end diameter larger than its distal end diameter.

* * * * *